United States Patent [19]

Ohtsu et al.

[11] Patent Number: 5,580,377
[45] Date of Patent: Dec. 3, 1996

[54] PLATE BARIUM SULFATE AND PROCESS FOR PRODUCING THE SAME

[75] Inventors: Koichi Ohtsu, Fukushima; Hirobumi Yoshida, Ibaraki; Noriaki Sato, Fukushima, all of Japan

[73] Assignee: Sakai Chemical Industry Co., Ltd., Osaka, Japan

[21] Appl. No.: 479,772

[22] Filed: Jun. 7, 1995

[30] Foreign Application Priority Data

Jun. 13, 1994 [JP] Japan ................................. 6-155308
Apr. 11, 1995 [JP] Japan ................................. 7-111218

[51] Int. Cl.$^6$ ........................................................ C09C 1/02
[52] U.S. Cl. ............................ 106/461; 106/415; 423/554; 423/638; 424/69; 424/401; 424/489; 424/78.03; 424/709; 424/722
[58] Field of Search ............................ 106/415, 461; 423/544, 554, 638; 424/69, 401, 489, 78.03, 709, 722

[56] References Cited

U.S. PATENT DOCUMENTS

| 3,915,661 | 10/1975 | Vichr | 423/263 |
|---|---|---|---|
| 4,128,630 | 12/1978 | Hayashi et al. | 424/69 |
| 4,894,093 | 1/1990 | Aderhold et al. | 106/461 |
| 5,171,572 | 12/1992 | Suganuma et al. | 106/461 |
| 5,246,687 | 9/1993 | Gorre et al. | 106/461 |

FOREIGN PATENT DOCUMENTS

| A10354609 | 2/1990 | European Pat. Off. . |
|---|---|---|
| A10445785 | 9/1991 | European Pat. Off. . |
| 61-191607 | 8/1986 | Japan . |
| 045215 | 1/1992 | Japan . |
| 0441411 | 2/1992 | Japan . |
| 0492630 | 4/1994 | Japan . |
| 6092630 | 7/1994 | Japan . |

OTHER PUBLICATIONS

Chemical Abstracts, vol. 104, No. 6, Feb. 10, 1986, abstract No. 36324p.

*Primary Examiner*—Mark L. Bell
*Assistant Examiner*—Michael Marcheschi
*Attorney, Agent, or Firm*—Sughrue, Mion, Zinn, Macpeak & Seas

[57] ABSTRACT

A plate barium sulfate is described, which has a particle size of from 1 to 100 µm or from 5 to 150 µm, wherein neither a sulfide nor a soluble barium salt is detected by an analysis method based on the Japanese Cosmetics Material Standard. The process of the plate barium sulfate is also described.

2 Claims, No Drawings

PLATE BARIUM SULFATE AND PROCESS FOR PRODUCING THE SAME

FIELD OF THE INVENTION

The present invention relates to a plate barium sulfate, a cosmetic composition comprising the plate barium sulfate and a process for producing the plate barium sulfate.

BACKGROUND OF THE INVENTION

As an extender pigment in cosmetics, in general, scaly powders such as talc, mica and sericite have been conventionally used. Particles in the form of scale are suitable for the use in make-up cosmetics because of their good extensibility, namely, slipperiness on skin and very pleasant feeling at use.

However, since these powders are obtained by crushing natural minerals, they have a color of grey or brown due to impurities present in their lattices. Accordingly, the original scaly powder color disadvantageously remains when the powders are compounded in cosmetics.

Also, since these powders are natural products, it is difficult to secure minerals having stable properties in a sufficiently enough amount and in particular, sericite has become hardly available. Mica can be procured relatively easily; however, because of its cleavage property, the mica cannot keep the form of scaly powder stably as a matter of defect.

Accordingly, techniques have been proposed for applying to cosmetics scaly powders of barium sulfate which is easily chemically synthesized.

JP-B-62-34688 (the term "JP-B" as used herein means an "examined Japanese patent publication") discloses a process for producing plate barium sulfates having a uniform particle size by reacting barium sulfide with sulfuric acid at a molar ratio of 1:1. However, according to this method, the barium sulfates are obtained in the form of a coarse particle. Although they may be suitable for the application to additives for synthetic resins or the like, the use in cosmetics cannot always be satisfied.

JP-A-3-257016 (the term "JP-A" as used herein means an "unexamined published Japanese patent application") discloses a process for producing plate barium sulfates having an aspect ratio of from 5 to 100 and a ratio of the square of the peripheral length to the area of the orthogonal projection face of the plate surface of from 20:1 to 150:1 by reacting a soluble barium salt with a sulfate. This process relates to plate barium sulfates for use in cosmetics having excellent use feeling and transparency but is accompanied by a doubt of deleteriousness to a human body, in particular, the skin. Also, the resulting plate barium sulfates cannot satisfy the slipperiness as a requirement for cosmetics.

JP-A-6-92630 discloses a process for producing plate barium sulfates having a narrow particle size distribution and excellent optical properties by adding a slight amount of sparingly soluble fine crystals to react with a soluble barium salt and a sulfate. However, in this technique, no investigation is made on the deleteriousness to the skin. Although the transparency can be achieved, the touch, the feel and the like as properties required for cosmetics are not examined.

SUMMARY OF THE INVENTION

Under these circumstances, an object of the present invention is to solve the above-described problems in producing a plate barium sulfate.

This and other objects of the present invention have been attained by a plate barium sulfate having a particle size of from 1 to 100 µm, wherein neither a sulfide ($S^{2-}$) nor a soluble barium salt ($Ba^{2+}$) is detected by an analysis method based on the Japanese Cosmetics Material Standard.

Furthermore, this and other objects of the present invention have been attained by a plate barium sulfate having a particle size of from 5 to 150 µm, wherein neither a sulfide ($S^{2-}$) nor a soluble barium salt ($Ba^{2+}$) is detected by an analysis method based on the Japanese Cosmetics Material Standard.

Moreover, this and other objects of the present invention have been attained by a process for producing the above-described plate barium sulfate having a particle size of from 1 to 100 µm, which comprises the steps of (a) feeding a barium hydroxide solution in a concentration of 400 g/l or less and a sulfuric acid solution in a concentration of 1,000 g/l or less simultaneously as a reaction solution, and (b) reacting these solutions while controlling an unreacted ion concentration in the reaction solution to from 0.00001 to 0.005 mol/l.

In addition, this and other objects of the present invention have been attained by a process for producing the above-described plate barium sulfate having a particle size of from 5 to 150 µm, which comprises the steps of (a) feeding a barium hydroxide solution in a concentration of 400 g/l or less and a sulfuric acid solution in a concentration of 1,000 g/l or less simultaneously as a reaction solution, (b) adding to the reaction solution a plate barium sulfate having a particle size of from 3 to 70 µm as a seed in an amount of from 5 to 90 wt % based on a total amount of the produced plate barium, and (c) reacting these solutions while controlling an unreacted ion concentration in the reaction solution to from 0.00001 to 0.005 mol/l.

DETAILED DESCRIPTION OF THE INVENTION

The present invention will be described in detail below.

The plate (tabular) barium sulfate of the present invention has properties such that a sulfide ($S^{2-}$) is not detected according to the analysis based on the Japanese Cosmetic Material Standard. The sulfide ($S^{2-}$) has toxicity to a human body, in particular, the skin. If the sulfide is present to such an extent that it can be detected by the above-described analysis, the plate barium sulfate cannot be used as cosmetics. Accordingly, in the plate barium sulfate of the present invention, it is required that the sulfide cannot be detected according to the above-described analysis. The analysis conducted as follows. To 10 g of obtained barium sulfate is added 10 ml of hydrochloric acid, and water is then added thereto up to 100 ml. The barium sulfate solution is then boiled for 10 minutes. Wet lead acetate paper is left in the gas generated with the boiling. If there is a sulfide, the wet lead acetate paper is blackened. Since the wet lead acetate paper is not blackened if the barium sulfate according to the present invention is used, a sulfide does not exist in the barium sulfate. Thus, the barium sulfate according to the present invention does not contain a sulfide.

The plate barium sulfate of the present invention has properties such that a soluble barium salt ($Ba^{2+}$) is not detected according to the analysis based on the Japanese Cosmetic Material Standard. The soluble barium salt ($Ba^{2+}$) has toxicity to a human body, in particular, the skin. If the soluble barium salt is present to such an extent that it can be detected by the above-described analysis, the plate barium sulfate cannot be used as cosmetics. Accordingly, in the plate barium sulfate of the present invention, it is required that the soluble barium salt cannot be detected according to the above-described analysis. The analysis is conducted as follows. The above-described barium sulfate solution is cooled, and water is then added thereto up to 100 ml. The solution is filtered off, and 50 ml of the filtrate is evaporated to dryness on a water bath. To the residue are added 2 drops of hydrochloric acid and 20 ml of warm water, and the obtained solution is filtered off with filter paper (No. 5C). The residue is washed with 10 ml of warm water, and the washing solution is added to the filtrate and then evaporated to dryness on a water bath. The residue is dried at a temperature of 105° C. for 1 hour, and 10 ml of water is then added thereto. The obtained solution is filtered off, and 0.5 ml of diluted sulfuric acid is added to the obtained filtrate and then left for 30 minutes. If there is a soluble barium salt, the solution becomes muddy. Since the obtained solution does not become muddy if the barium sulfate according to the present invention is used, a soluble barium salt does not exist in the barium sulfate. Thus, the barium sulfate according to the present invention does not contain a soluble barium salt.

Among the plate barium sulfates of the present invention, if a plate barium sulfate produced by a process comprising the steps of feeding a barium hydroxide solution in a concentration of 400 g/l or less and a sulfuric acid solution in a concentration of 1,000 g/l or less simultaneously and reacting these solutions while controlling the unreacted ion concentration in the reaction solution to from 0.00001 to 0.005 mol/l, the plate barium sulfate obtained has a particle size of from 1 to 100 μm, preferably from 3 to 70 μm. In this method, if the particle size is less than 1 μm, the slipperiness is conspicuously impaired; whereas if it exceeds 100 μm, the touch is rough. In either case, cosmetics cannot be put into practical use, thus the particle size is limited to fall in the above-described range.

Among the plate barium sulfates of the present invention, if a plate barium sulfate produced by adding a plate barium sulfate having a particle size of from 3 to 70 μm, preferably from 10 to 30 μm, as a seed into the reaction solution in an amount of from 5 to 90 wt % (% by weight), preferably from 30 to 70 wt %, based on the total weight of the produced plate barium sulfate before the above-described reaction of a barium hydroxide solution and a sulfuric acid solution, the plate barium sulfate obtained has a particle size of from 5 to 150 μm, preferably from 20 to 100 μm. If the particle size is less than 5 μm, the slipperiness is conspicuously impaired; whereas if it exceeds 150 μm, the touch is rough. In either case, cosmetics cannot be put into practical use, thus the particle size is limited to fall in the above-described range.

The term "plate barium sulfate" as used in the present invention means single particles, in which a ratio of the minimum length in the plane direction of the barium sulfite particle to the thickness direction taken as 1 is 5 or more.

The particle size of the plate barium sulfates of the present invention is obtained by averaging the maximum sizes of 20 barium sulfate particles present on a straight line randomly drawn on an electron microscopic photograph.

The plate barium sulfates of the present invention can exert the effect peculiar to the present invention when they are used mainly for cosmetics.

If the plate barium sulfates are used as a cosmetic composition, they may be used together with a cosmetically acceptable carrier.

The plate barium sulfates of the present invention can be produced by reacting barium hydroxide with sulfuric acid.

The plate barium sulfates have been usually produced by reacting a soluble barium salt (e.g., barium sulfide, barium nitrate) and a soluble sulfate (e.g., sodium sulfate, ammonium sulfate); however, in any case, by-products such as barium sulfide and ammonium nitrate are produced in the plate barium sulfate particle and it has been difficult to separate and remove them completely.

According to the present invention, produced other than the barium sulfate is only water and this is very beneficial in industrial viewpoint. Also, in the present invention, because purified raw materials are used, barium sulfate of very high purity can be obtained and thereby the objects of the present invention can be achieved.

The above-described reaction may be conducted in either a continuous system or a batch system. In either system, the barium hydroxide and the sulfuric acid in chemical equivalent are continuously fed at the same time to a reaction vessel with a stirrer and reacted.

In the above-described reaction solution, the unreacted barium ion concentration and the sulfuric acid ion concentration are each controlled to from 0.00001 to 0.005 mol/l. It is very difficult to control the concentration to less than 0.00001 mol/l, and if it exceeds 0.005 mol/l, the plate barium sulfate particle cannot be produced.

Since a correlation as shown in Table 1 below is present between the unreacted ion concentration and the conductivity, the above-described unreacted ion concentration can be controlled by controlling the addition amount so that the conductivity can be maintained at a constant value.

TABLE 1

| Unreacted Ion Concentration (mol/l) | Conductivity (μS) | Particle Size (μm) |
| --- | --- | --- |
| 0.00001–0.00005 | 1–50 | 20–70 |
| 0.00005–0.0005 | 50–500 | 5–30 |
| 0.0005–0005 | 500–5,000 | 3–10 |

In the method of the present invention, the barium hydroxide solution fed to a reaction vessel each has a concentration of 400 g/l or less, preferably from 1 to 400 g/l, and the sulfuric acid solution fed to a reaction vessel has a concentration of 1,000 g/l or less, preferably from 1 to 1,000 g/l. If the concentrations exceed the above upper limits, the ion concentration of unreacted materials cannot be precisely controlled, thus, the concentration is limited to fall in the above-described range. Too much thin concentration is disadvantageous in industrial viewpoint and the concentrations are, therefore, each preferably from 10 to 200 g/l.

The reaction temperature is preferably from 0° to 100° C., and more preferably from 0° to 80° C. If it exceeds 100° C., the particles grow conspicuously in the thickness direction and fail to give slippery touch, and as a result, they becomes unsuited for cosmetics.

In the method of the present invention, after the completion of the reaction, barium hydroxide or sulfuric acid is preferably added to adjust the pH of the reaction solution to fall in the range of from 6.5 to 7.5. This operation can restrict the by-product only to water and therefore, the sulfide ($S^{2-}$) and soluble barium salt ($Ba^{2+}$) contents can be reduced to such an extent that they cannot be detected according to the analysis based on the Japanese Cosmetics Material Standard.

Another feature of the present invention is to provide a plate barium sulfate having a good touch property even if it has a particle size of from 5 to 150 μm. This plate barium sulfate can be produced by adding a plate barium sulfate having a particle size of from 3 to 70 μm as a seed to the reaction solution in an amount of from 5 to 90 wt % based on the total amount of the produced plate barium sulfate before the reaction of a barium hydroxide solution and a sulfuric acid solution.

The thus-produced plate barium sulfate has a very good touch even if it has a particle size exceeding 100 μm and can be used with much satisfaction as a plate barium sulfate for cosmetics.

The present invention will be described below in greater detail with reference to the following examples but the present invention should not be construed as being limited thereto.

EXAMPLE 1

Preparation of Barium Sulfate

Pure water of 70° C. filled up a reaction vessel which overflows at 3 l and was continuously stirred. Separately, 65 g/l (0.663 mol/l) of dilute sulfuric acid adjusted to 70° C. and 35 g/l (0.204 mol/l) of a barium hydroxide solution adjusted to 70° C. were continuously added at the same time to the reaction vessel above by means of a microtube pump capable of fine adjustment.

At this time, the flow rate of the dilute sulfuric acid was fixed to 120 ml/min and while continuously measuring the conductivity of the slurry overflowed, the flow rate of the barium hydroxide solution was controlled to give an conductivity of 30 μS (the unreacted ion concentration: about 0.00003 mol/l) or less. At the time when the conductivity of the slurry was stabilized to 30 μS, the flow rate of the barium hydroxide solution was 390 ml/min.

Ten minutes after the initiation of reaction, about 500 ml of the reaction solution was withdrawn. The reaction solution had a pH of about 4.0. A barium hydroxide solution (0.1 mol/l) was added thereto to adjust the pH to 6.5. The resulting solution was filtered and dried at 120° C. to obtain white barium sulfate powders.

Measurement of Particle Size

The resulting barium sulfate powders were observed through a scanning electron microscope and identified to be plate particles. An average of the maximum sizes of respective 20 particles present on a straight line randomly drawn on the electron microscopic photograph was taken as a particle size of the resulting particles. The results obtained are shown in Table 2.

Verification of Soluble Sulfide and Barium Salt in Barium Sulfate Particle

In order to examine whether soluble sulfide and barium salt were contained in the barium sulfate particle, $S^{2-}$ and $Ba^{2+}$ generated from these compounds were examined by the analysis based on the Japanese Cosmetics Material Standard but they were not detected.

Touch

Seven panelists each picked the resulting barium sulfate powder with fingers and reported on the slipperiness at rubbing and the touch was evaluated by the average value of their estimation. The results obtained are shown in Table 2.

EXAMPLE 2

White barium sulfate powders were prepared in the same manner as in Example 1, except that 130 g/l (1.327 mol/l) of dilute sulfuric acid adjusted to 25° C. and 70 g/l (0.408 mol/l) of a barium hydroxide solution adjusted to 25° C. were used and the conductivity of the reacted slurry was controlled to 300 μS. The particle size and the touch were determined and evaluated in the same manner as in Example 1 and the results obtained are shown in Table 2.

EXAMPLE 3

White barium sulfate powders were prepared in the same manner as in Example 1, except for controlling the conductivity of the reacted slurry to 700 μS. The particle size and the touch were determined and evaluated in the same manner as in Example 1 and the results obtained are shown in Table 2.

EXAMPLE 4

A reaction was conducted in the same manner as in Example 2 and 1 l of the resulting slurry was divided and transferred to a 5-l glass beaker. Pure water (1 l) was added thereto and heated while stirring continuously and the temperature was kept at 50° C. Separately, 65 g/l (0.663 mol/l) of a barium hydroxide solution adjusted to 50° C. was continuously added to the reaction vessel above kept at a temperature of 50° C. by means of a microtube pump capable of fine adjustment. At this time, the flow rate of the dilute sulfuric acid was fixed to 5 ml/min and while continuously measuring the conductivity of the reacted slurry, the flow rate of the barium hydroxide solution was controlled to give the conductivity of 300 μS or less. The reaction was continued until the total liquid amount in the reaction vessel reached 4 l and then the solution was filtered and dried at 120° C. to obtain white barium sulfate powders. The particle size and the touch of the resulting barium sulfate powders were determined and evaluated in the same manner as in Example 1 and the results obtained are shown in Table 2.

COMPARATIVE EXAMPLES 1 AND 2

Mica (Comparative Example 1) or talc (Comparative Example 2) as an extender pigment for cosmetics was used and the particle size and the touch were determined and evaluated in the same manner as in Example 1. The results obtained are shown in Table 2.

TABLE 2

| Example No. | Particle Size (μm) | Touch |
| --- | --- | --- |
| Example 1 | 70 | Good |
| Example 2 | 30 | Very Good |
| Example 3 | 3 | Good |
| Example 4 | 85 | Very Good |
| Comparative Example 1 | 20 | Good |
| Comparative Example 2 | 18 | Good |

The plate barium sulfates of the present invention do not contain detectable, harmful sulfide or soluble barium salt in the particle and have good touch, thus, they can be good plate barium sulfates for cosmetics.

While the invention has been described in detail and with reference to specific embodiments thereof, it will be apparent to one skilled in the art that various changes and modifications can be made therein without departing from the spirit and scope thereof.

What is claimed is:

1. A process for producing a plate barium sulfate having a particle size of from 1 to 100 μm, wherein neither a sulfide nor a soluble barium salt is detected by an analysis method based on the Japanese Cosmetics Material Standard, which comprises the steps of (a) feeding a barium hydroxide solution in a concentration of 400 g/l or less and a sulfuric acid solution in a concentration of 1,000 g/l or less simultaneously as a reaction solution, and (b) reacting these solutions while controlling an unreacted ion concentration in the reaction solution to from 0.00001 to 0.005 mol/l.

2. A process for producing a plate barium sulfate having a particle size of from 5 to 150 μm, wherein neither a sulfide nor a soluble barium salt is detected by an analysis method based on the Japanese Cosmetics Material Standard, which comprises the steps of (a) feeding a barium hydroxide solution in a concentration of 400 g/l or less and a sulfuric acid solution in a concentration of 1,000 g/l or less simultaneously as a reaction solution, (b) adding to the reaction solution a plate barium sulfate having a particle size of from 3 to 70 μm as a seed in an amount of from 5 to 90 wt % based on a total amount of the produced plate barium, and (c) reacting these solutions while controlling an unreacted ion concentration in the reaction solution to from 0.00001 to 0.005 mol/l.

* * * * *